United States Patent
Peultier et al.

(10) Patent No.: US 11,484,349 B2
(45) Date of Patent: Nov. 1, 2022

(54) SURGICAL SYSTEM AND METHOD

(71) Applicant: Warsaw Orthopedic, Inc., Warsaw, IN (US)

(72) Inventors: Bertrand Peultier, Les Hopitaux Neufs (FR); Loïc Josse, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 67 days.

(21) Appl. No.: 16/487,064

(22) PCT Filed: Feb. 17, 2017

(86) PCT No.: PCT/IB2017/000290
§ 371 (c)(1),
(2) Date: Aug. 19, 2019

(87) PCT Pub. No.: WO2018/150215
PCT Pub. Date: Aug. 23, 2018

(65) Prior Publication Data
US 2020/0054362 A1 Feb. 20, 2020

(51) Int. Cl.
*A61B 17/70* (2006.01)
*A61B 17/00* (2006.01)
*A61B 17/68* (2006.01)

(52) U.S. Cl.
CPC ........ *A61B 17/708* (2013.01); *A61B 17/7086* (2013.01); *A61B 2017/00407* (2013.01); *A61B 2017/681* (2013.01)

(58) Field of Classification Search
CPC ............ A61B 17/7074; A61B 17/7077; A61B 17/7079; A61B 17/708; A61B 17/7083; A61B 17/7085; A61B 17/7091
See application file for complete search history.

(56) References Cited

U.S. PATENT DOCUMENTS

| | | | | |
|---|---|---|---|---|
| 7,666,189 B2 * | 2/2010 | Gerber | ............... | A61B 17/7083 606/86 A |
| 8,038,699 B2 * | 10/2011 | Cohen | ................ | A61B 17/7076 606/246 |
| 8,100,828 B2 * | 1/2012 | Frey | ................... | A61B 17/7077 600/234 |
| 8,137,356 B2 * | 3/2012 | Hestad | ............... | A61B 17/7085 606/86 A |

(Continued)

OTHER PUBLICATIONS

International Search Report for PCT/IB2017/000290 date of completion is Oct. 31, 2019 (3 pages).

(Continued)

*Primary Examiner* — Lynnsy M Summitt
(74) *Attorney, Agent, or Firm* — Sorell, Lenna & Schmidt, LLP

(57) ABSTRACT

A surgical system comprises at least one implant support including a first implant support that is engageable with a receiver of a first fastener having a shaft fixed with vertebral tissue. At least one adaptor includes a first adaptor extending longitudinally along and being engageable with the first implant support. The first adaptor is rotatable relative to the first implant support to connect the first implant support with a surgical instrument to manipulate the vertebral tissue. Surgical instruments, constructs, implants and methods are disclosed.

20 Claims, 14 Drawing Sheets

(56) References Cited

U.S. PATENT DOCUMENTS

| | | | | |
|---|---|---|---|---|
| 8,221,426 B2* | 7/2012 | Justis | A61B 17/708 | 606/86 A |
| 8,357,184 B2* | 1/2013 | Woolley | A61B 17/7077 | 606/279 |
| 8,460,308 B2* | 6/2013 | Marino | A61B 17/7037 | 606/104 |
| 8,475,467 B2* | 7/2013 | Manninen | A61B 17/7079 | 606/105 |
| 8,617,218 B2* | 12/2013 | Justis | A61B 17/7085 | 606/86 A |
| 8,672,944 B2* | 3/2014 | Boachie-Adjei | A61B 17/7076 | 606/86 A |
| 8,702,713 B2* | 4/2014 | Nayet | A61B 17/708 | 606/86 A |
| 8,747,409 B2* | 6/2014 | Ichelmann | A61B 17/7085 | 606/86 R |
| 8,834,485 B2* | 9/2014 | Kave | A61B 17/7074 | 606/102 |
| 8,900,237 B2* | 12/2014 | Ramsay | A61B 17/7085 | 606/86 A |
| 8,906,034 B2* | 12/2014 | Gleeson | A61B 17/7074 | 606/99 |
| 8,951,257 B2* | 2/2015 | Lenke | A61B 17/708 | 606/86 A |
| 8,992,536 B2* | 3/2015 | Piza Vallespir | A61B 17/708 | 606/86 A |
| 9,005,204 B2* | 4/2015 | Manninen | A61B 17/7037 | 606/86 A |
| 9,066,761 B2* | 6/2015 | McBride | A61B 17/708 | |
| 9,101,401 B2* | 8/2015 | Dalton | A61B 17/7032 | |
| 9,101,412 B2* | 8/2015 | Bootwala | A61B 17/7077 | |
| 9,179,957 B2* | 11/2015 | Ibrahim | A61B 17/7091 | |
| 9,204,909 B2* | 12/2015 | Rezach | A61B 17/7085 | |
| 9,211,149 B2* | 12/2015 | Hoefer | A61B 17/7083 | |
| 9,241,742 B2* | 1/2016 | Stad | A61B 17/7077 | |
| 9,314,273 B2* | 4/2016 | Iott | A61F 2/4611 | |
| 9,314,281 B2* | 4/2016 | Beger | A61B 90/57 | |
| 9,402,660 B2* | 8/2016 | Brinkman | A61B 17/7077 | |
| 9,468,474 B2* | 10/2016 | Parikh | A61B 17/7086 | |
| 9,480,504 B1* | 11/2016 | Schafer | A61B 17/7083 | |
| 9,480,505 B2* | 11/2016 | Hutchens | A61B 17/7086 | |
| 9,510,875 B2* | 12/2016 | Reitblat | A61B 17/708 | |
| 9,561,062 B2* | 2/2017 | Hayes | A61B 17/025 | |
| 9,795,417 B2* | 10/2017 | Beger | A61B 17/7032 | |
| 9,907,582 B1* | 3/2018 | Olea | A61B 17/60 | |
| 10,111,650 B2* | 10/2018 | Nel | A61B 17/02 | |
| 10,159,579 B1* | 12/2018 | Reitblat | A61B 17/70 | |
| 10,278,687 B2* | 5/2019 | Cryder | A61B 17/025 | |
| 10,299,838 B2* | 5/2019 | Biester | A61B 17/7074 | |
| 10,390,862 B2* | 8/2019 | Bobbitt | A61B 17/7032 | |
| 10,398,454 B2* | 9/2019 | Patrinicola | A61B 17/7043 | |
| 10,492,837 B2* | 12/2019 | Farmer | A61B 17/7091 | |
| 10,588,673 B2* | 3/2020 | Fischer | A61B 17/7079 | |
| 10,617,449 B2* | 4/2020 | Corbin | A61B 17/7077 | |
| 10,772,662 B2* | 9/2020 | Rezach | A61B 17/7077 | |
| 10,898,239 B2* | 1/2021 | Olea | A61B 17/7079 | |
| 10,945,773 B2* | 3/2021 | Medeiros | A61B 17/0206 | |
| 2005/0245928 A1* | 11/2005 | Colleran | A61B 17/708 | 606/90 |
| 2008/0077155 A1* | 3/2008 | Diederich | A61B 17/708 | 606/105 |
| 2008/0119852 A1* | 5/2008 | Dalton | A61B 17/7032 | 606/86 R |
| 2008/0125788 A1* | 5/2008 | Cohen | A61B 17/708 | 606/104 |
| 2008/0154280 A1 | 6/2008 | Schumacher et al. | | |
| 2009/0204159 A1* | 8/2009 | Justis | A61B 17/708 | 606/323 |
| 2012/0035611 A1* | 2/2012 | Kave | A61B 17/7074 | 606/102 |
| 2012/0116467 A1* | 5/2012 | King | A61B 17/708 | 606/86 A |
| 2012/0197309 A1* | 8/2012 | Steele | A61B 17/7085 | 606/301 |
| 2013/0211453 A1* | 8/2013 | Lenke | A61B 17/7077 | 606/250 |
| 2013/0245692 A1 | 9/2013 | Hayes et al. | | |
| 2013/0304130 A1* | 11/2013 | Jackson | A61B 17/7085 | 606/278 |
| 2014/0039557 A1* | 2/2014 | Stad | A61B 17/7077 | 606/279 |
| 2014/0039567 A1* | 2/2014 | Hoefer | A61B 17/7082 | 606/86 A |
| 2014/0052197 A1* | 2/2014 | McBride | A61B 17/708 | 606/86 A |
| 2014/0058464 A1* | 2/2014 | Hutchens | A61B 17/7091 | 606/86 A |
| 2014/0107707 A1* | 4/2014 | Rovner | A61B 17/7002 | 606/264 |
| 2014/0228899 A1* | 8/2014 | Thoren | A61B 17/7077 | 606/86 R |
| 2014/0275793 A1* | 9/2014 | Song | A61B 17/7001 | 600/204 |
| 2014/0277168 A1* | 9/2014 | Hutton | A61B 17/7032 | 606/279 |
| 2014/0311264 A1* | 10/2014 | Black | A61B 17/7085 | 74/89.23 |
| 2015/0045834 A1* | 2/2015 | McBride | A61B 17/7077 | 606/264 |
| 2015/0066088 A1* | 3/2015 | Brinkman | A61B 17/7077 | 606/264 |
| 2015/0164569 A1 | 6/2015 | Reitblat et al. | | |
| 2016/0089188 A1* | 3/2016 | McBride, Jr | A61B 17/7089 | 606/279 |
| 2016/0262807 A1 | 9/2016 | Benson et al. | | |
| 2018/0153585 A1* | 6/2018 | Levine | A61B 17/1655 | |
| 2019/0090864 A1* | 3/2019 | Medeiros | A61B 17/29 | |
| 2019/0090908 A1* | 3/2019 | Stad | A61B 17/7002 | |
| 2019/0142470 A1* | 5/2019 | Kim | A61B 17/7007 | 606/246 |
| 2019/0183541 A1* | 6/2019 | Lee | A61B 17/7083 | |
| 2019/0216453 A1* | 7/2019 | Predick | A61B 17/025 | |
| 2019/0231394 A1* | 8/2019 | Bechtel | A61B 17/025 | |
| 2019/0290330 A1* | 9/2019 | Combrowski | A61F 2/4611 | |
| 2019/0290335 A1* | 9/2019 | Biester | A61B 17/025 | |
| 2020/0038074 A1* | 2/2020 | Hutchens | A61B 17/7085 | |
| 2020/0054361 A1* | 2/2020 | Peultier | A61B 17/7085 | |
| 2020/0054362 A1* | 2/2020 | Peultier | A61B 17/7086 | |
| 2020/0107302 A1* | 4/2020 | Biedermann | A61B 17/7032 | |
| 2020/0297394 A1* | 9/2020 | Schafer | A61B 17/708 | |
| 2020/0315663 A1* | 10/2020 | Manninen | A61B 17/7079 | |

OTHER PUBLICATIONS

China National Intellectual Property Administration, Application/Patent No. 201780086033.4, Notice on the First Office Action, Date of Dispatch: Jan. 14, 2022.

China National Intellectual Property Administration (CNIPA) Application/Patent No. 201780086033.4, Notice on the Second Office Action, Date of Dispatch: Aug. 29, 2022.

* cited by examiner

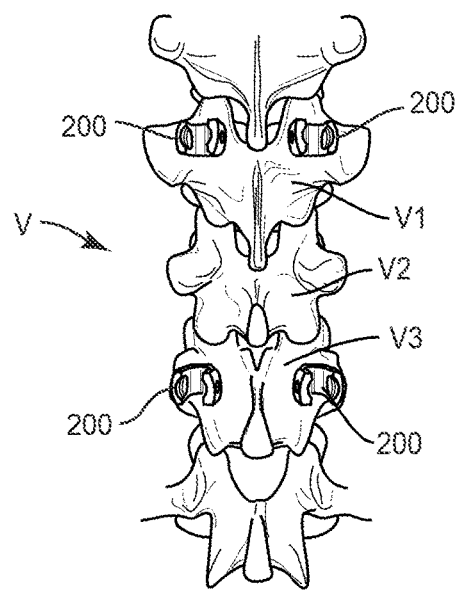 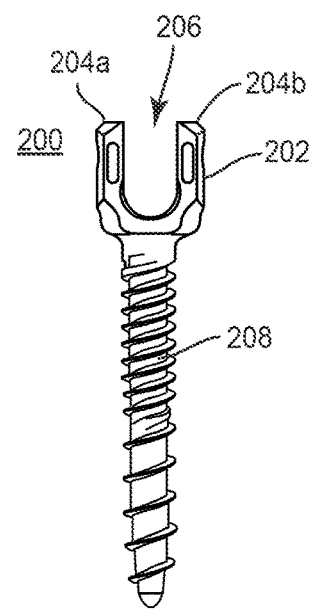 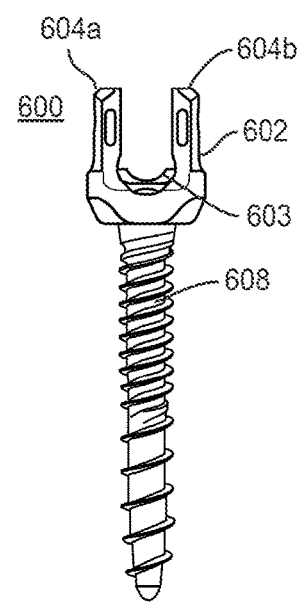
*FIG. 7*  *FIG. 9*  *FIG. 10*
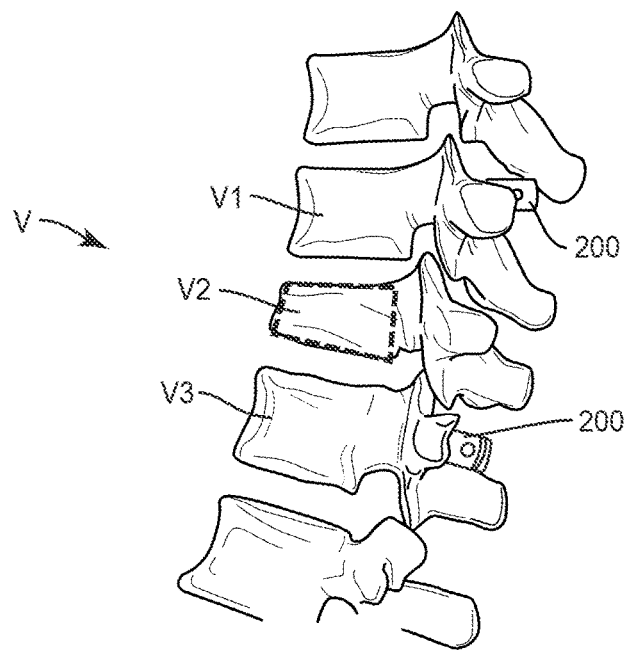
*FIG. 8*

SURGICAL SYSTEM AND METHOD

CROSS-REFERENCE TO RELATED APPLICATION

This application is a National Stage Application of PCT/IB2017/000290 under 35USC § 371 (a), the disclosure of the above-identified application is hereby incorporated by reference in its entirety.

TECHNICAL FIELD

The present disclosure generally relates to medical devices for the treatment of spinal disorders, and more particularly to a surgical system and a method for correction of a spinal disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation and implantable prosthetics. Correction treatments used for positioning and alignment of vertebrae may employ spinal implants including spinal constructs and interbody devices for stabilization of a treated section of a spine. In some cases, the spinal implants may be manipulated with surgical instruments for compression and distraction of vertebrae. This disclosure describes an improvement over these prior technologies.

SUMMARY

In one embodiment, a surgical system is provided. The surgical system includes at least one implant support including a first implant support that is engageable with a receiver of a first fastener having a shaft fixed with vertebral tissue. At least one adaptor includes a first adaptor extending longitudinally along and being engageable with the first implant support. The first adaptor is rotatable relative to the first implant support to connect the first implant support with a surgical instrument to manipulate the vertebral tissue. In some embodiments, surgical instruments, constructs, implants and methods are disclosed.

BRIEF DESCRIPTION OF THE DRAWINGS

The present disclosure will become more readily apparent from the specific description accompanied by the following drawings, in which:

FIG. 7 is a plan view of components of one embodiment of a surgical system in accordance with the principles of the present disclosure disposed with vertebrae;

FIG. 8 is a side view of components of one embodiment of a surgical system in accordance with the principles of the present disclosure disposed with vertebrae;

FIG. 9 is a side view of components of one embodiment of a surgical system in accordance with the principles of the present disclosure;

FIG. 10 is a side view of components of one embodiment of a surgical system in accordance with the principles of the present disclosure;

DETAILED DESCRIPTION

Figure 1:
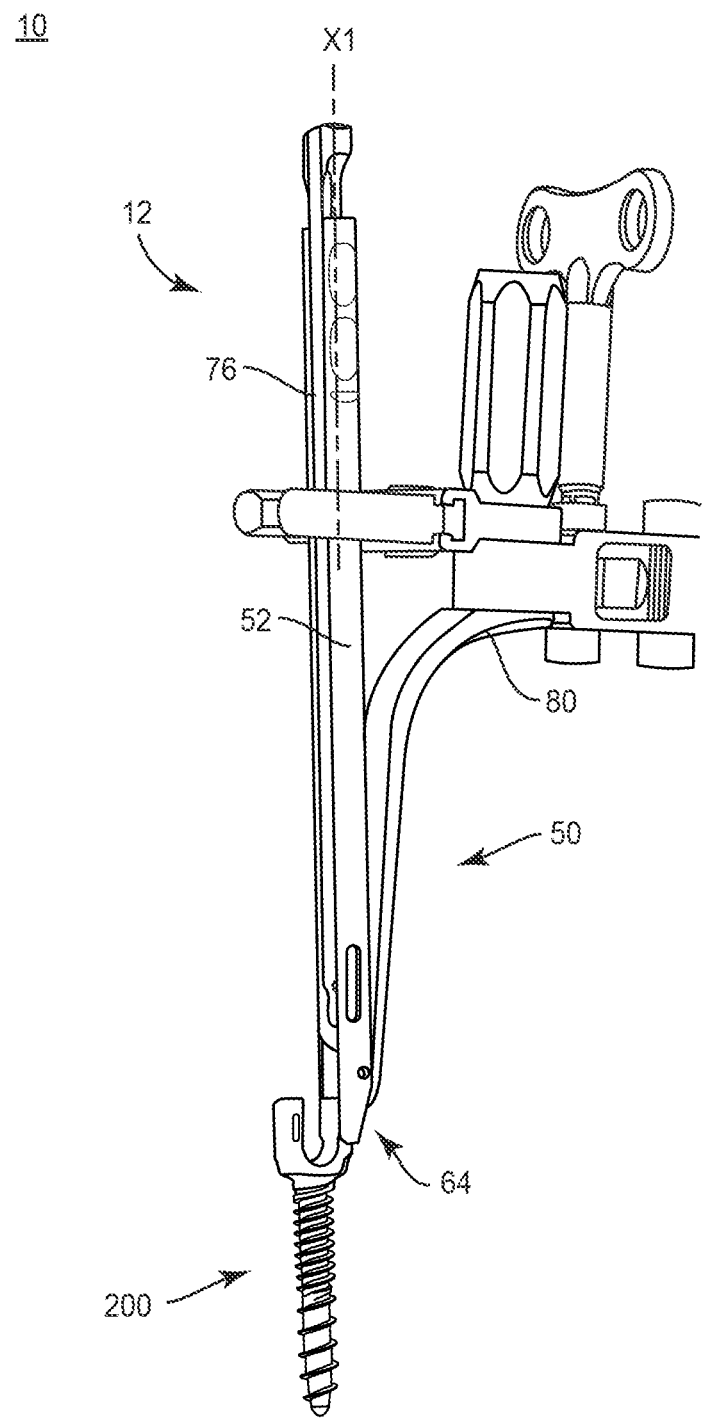
FIG. 1 is a side view of components of one embodiment of a surgical system in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system includes surgical instruments that allow vertebral manipulation to treat spinal disorders, as described herein, for managing lordosis and/or kyphosis restoration. In some embodiments, the surgical instruments allow for parallel distraction and/or compression of vertebral tissue.

In some embodiments, the present surgical system includes a trauma instrument. In some embodiments, the present surgical system is utilized with a method to correct complex spinal deformities. In some embodiments, the present surgical system is utilized with a method to treat degenerative spinal disorders and/or employed with transforaminal lumbar interbody fusion procedures. In some embodiments, the present surgical system is configured for utilization with sagittal adjusting screws (SAS), fixed axis screws (FAS) and/or multi-axial screws (MAS). In some embodiments, the present surgical system comprises a plurality of distractors, such as, for example, two distractors disposed along a side of vertebrae to perform a ligamentotaxy procedure. In some embodiments, the present surgical system comprises a single distractor to treat degenerative spinal disorders, for example, for disposal along a side of vertebrae oriented for decompression and/or interbody cage insertion.

In some embodiments, the present surgical system is employed with a surgical technique for an open approach procedure. In some embodiments, the present surgical system includes an implant support having a screw manipulation stick. In some embodiments, the implant support is positioned to provide access to a screw receiver to facilitate rod insertion. In some embodiments, the present surgical system includes an adaptor connected to the implant support with a pivot hinge disposed adjacent a connection point with the screw receiver. As such, an implant support connected with the screw receiver can include a point of rotation at the screw receiver level. In some embodiments, the present surgical system includes an implant support having an offset connection to a bone screw. In some embodiments, the present surgical system includes an implant support having a slide configured for translation to move the implant support between an open orientation and a closed orientation. In some embodiments, the present surgical system includes an alignment guide configured to facilitate location of the bone screw.

In some embodiments, the surgical system includes an adaptor connected with a surgical instrument and an angulation module having arms for connection with an implant support. In some embodiments, the angulation module is configured for individual angulation of implant supports in a range of +/−20 degrees. In some embodiments, a compressor/distractor is utilized for distraction and the angulation module maintains an angle of the extender with vertebrae. In some embodiments, the present surgical system is employed with a method including the steps of inserting the adaptor with an implant support at a surgical site and the step of sliding a sleeve along the implant support. In some embodiments, the method includes the step of securing the sleeve to the implant support. In some embodiments, the method includes the steps of connecting the implant support to the screws using the guide to facilitate alignment.

In some embodiments, the present surgical system is employed with a surgical technique including distraction of the posterior ligament. In some embodiments, the present surgical system is employed with a surgical technique for distracting vertebral tissue in a parallel configuration. In some embodiments, the present surgical system is employed with a surgical technique including correction of vertebral angle by manual manipulation of the implant support. In some embodiments, the angulation module is configured to maintain a corrected angle during manual manipulation of the implant support. In some embodiments, the present surgical system is employed with a surgical technique including contouring and insertion of a spinal rod. In some embodiments, the surgical system includes a rod reduction lever configured to reduce the spinal rod with the screws.

In some embodiments, the present surgical system includes a surgical instrument configured to compress or distract and restore curvature of a spine. In some embodiments, the present surgical system includes instruments and tools for correcting a sagittal deformity and rebalancing a spine of a body. In some embodiments, the present surgical system is employed to treat degenerative deformities of a spine in a sagittal plane, for example, degenerative kyphosis. In some embodiments, the present surgical system is employed to treat hyper-kyphosis and flat lumbar back, including disorders that create an unbalance of a body and loss of alignment between body parts. In some embodiments, the present surgical system provides a selected amount of correction to apply a selected balance to a spine and provides control and adjustment to the amount of correction. In some embodiments, the present surgical system includes a series of tools and instruments that allow formulation of a type of correction applied and can control the correction stabilization using posterior instrumentation.

In some embodiments, one or all of the components of the surgical system are disposable, peel-pack, pre-packed sterile devices used with a spinal construct. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including posterior, posterior mid-line, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are disclosed. Reference is made to the exemplary embodiments of the present disclosure, which are illustrated in the accompanying figures. Turning to FIGS. 1-6, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of surgical system 10 are configured for engagement with spinal constructs attached with vertebrae to manipulate tissue and/or correct a spinal disorder, such as, for example, a sagittal deformity, as described herein. In some embodiments, surgical system 10 may be employed with surgical procedures, such as, for example, corpectomy, discectomy and/or fracture/trauma treatment and may include fusion and/or fixation that employ implants to restore the mechanical support function of vertebrae.

Figure 6:
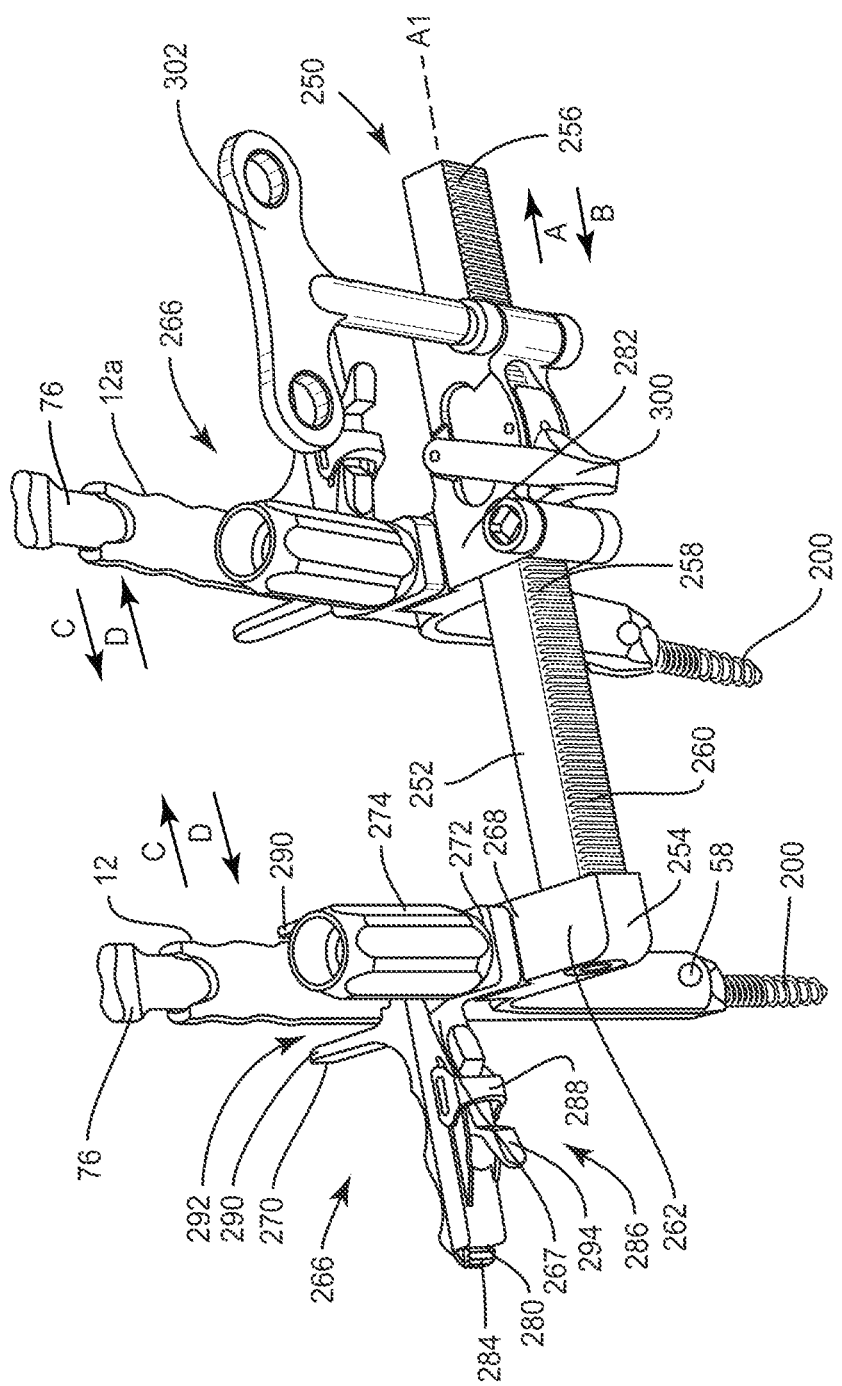
FIG. 6 is a perspective view of components of one embodiment of a surgical system in accordance with the principles of the present disclosure.
Figure 11:
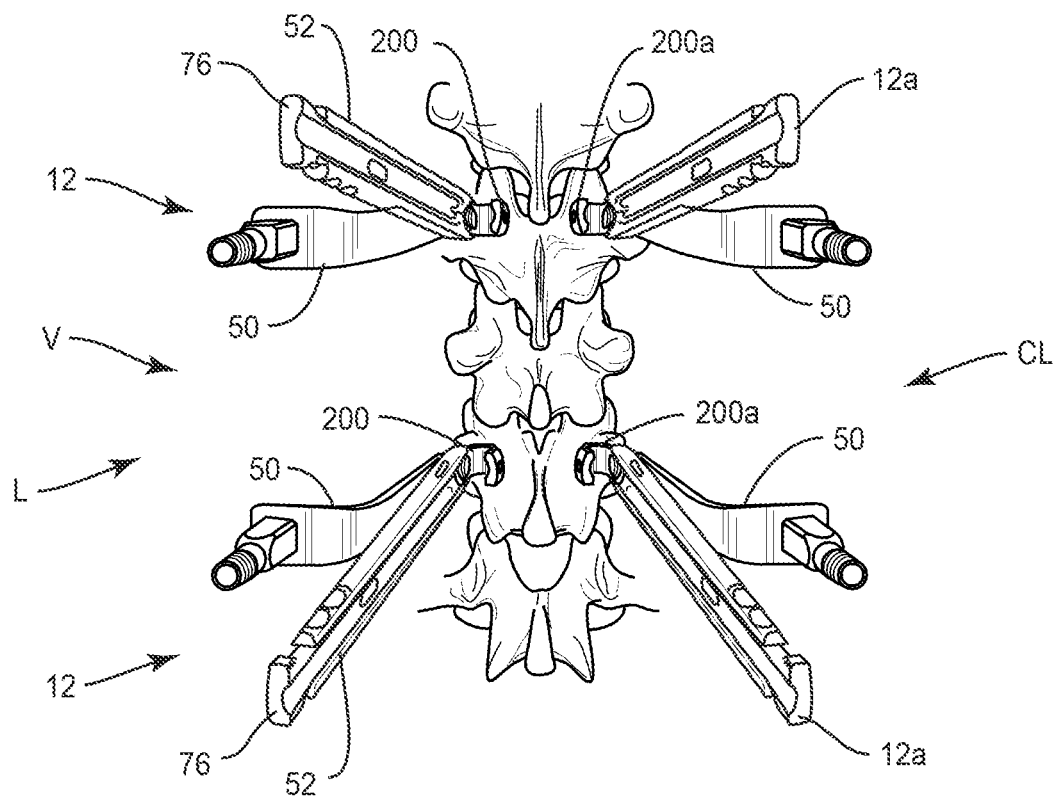
FIG. 11 is a plan view of components of one embodiment of a surgical system in accordance with the principles of the present disclosure disposed with vertebrae.
Figure 12:
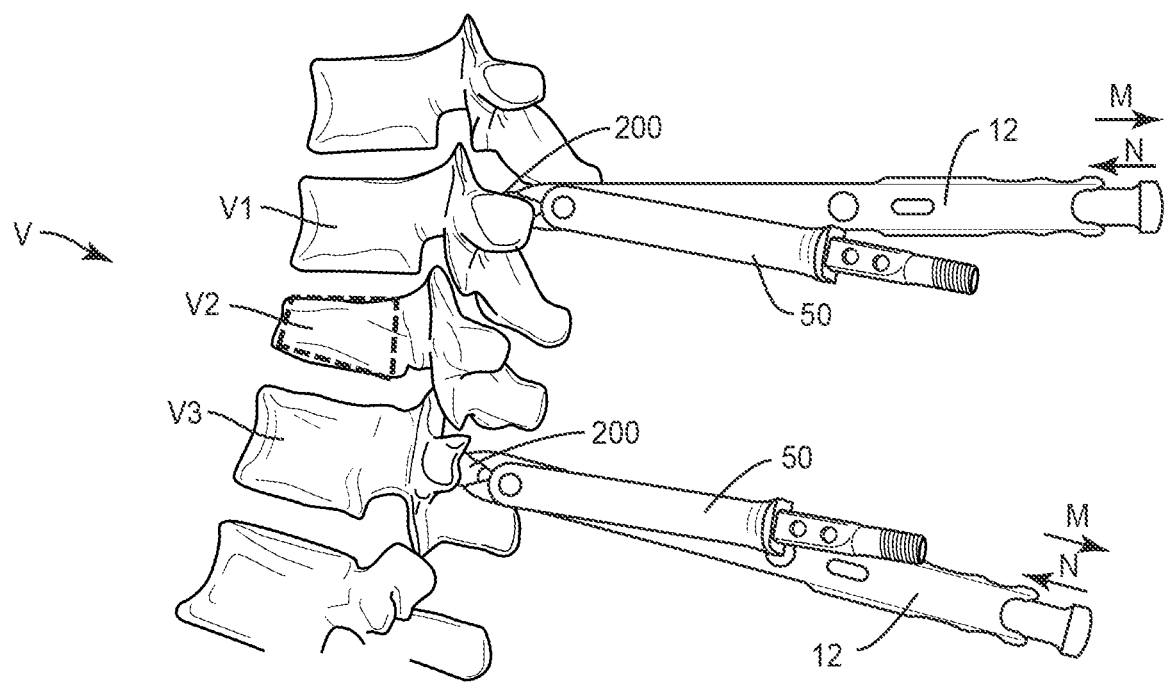
FIG. 12 is a side view of components of one embodiment of a surgical system in accordance with the principles of the present disclosure disposed with vertebrae.

Surgical system 10 includes implant supports, such as, for example, sticks 12. Sticks 12 are engageable with bone fasteners, such as, for example, FAS 200 and/or SAS 600, and a surgical instrument, such as, for example, a compressor/distractor 250 via adaptors 50 to manipulate tissue, as shown in FIG. 6 and described herein.

Figure 3:
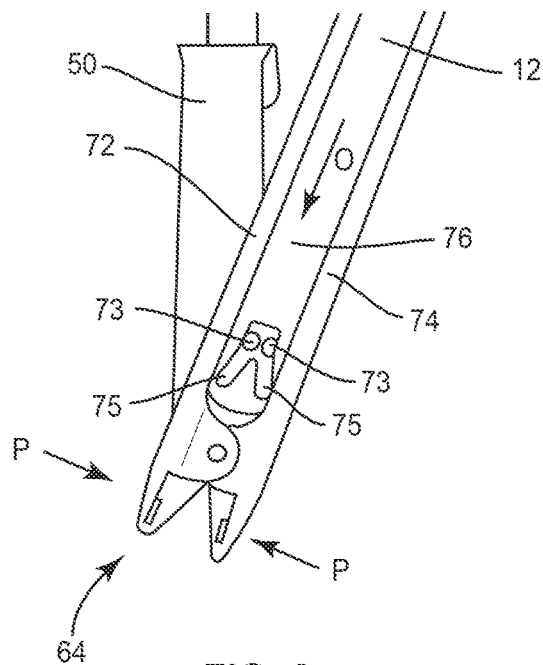
FIG. 3 is a side view of components of one embodiment of a surgical system in accordance with the principles of the present disclosure.
Figure 4:
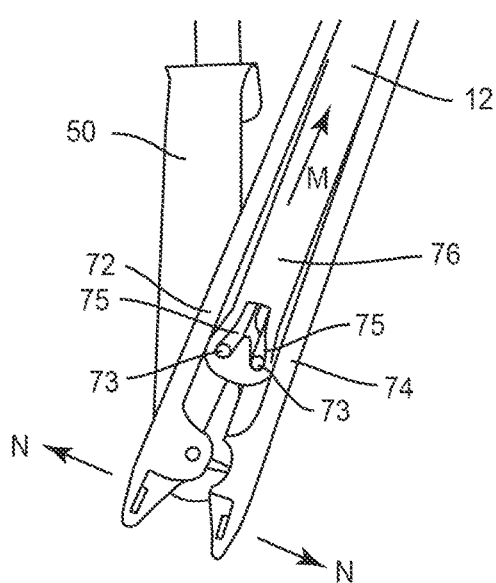
FIG. 4 is a side view of components of one embodiment of a surgical system in accordance with the principles of the present disclosure.

Stick 12 includes a body, such as, for example, a sleeve 52. Sleeve 52 extends along an axis X1, as shown in FIG. 1. Sleeve 52 includes an extension 72 and extension 74. Extensions 72, 74 are relatively moveable via relative translation of a translation element, such as, for example, a slide 76. Slide 76 is manipulated for translation within channel 62 to move extensions 72, 74 between an open orientation, as shown in FIG. 4, and a closed, capture orientation, as shown in FIG. 3. Slide 76 is translated, in a direction shown by arrow M in FIG. 4, to cause extensions 72, 74 to rotate and expand, in a direction shown by arrows N, to the open orientation. In the open orientation, pins 73 are seated in a bottom of slots 75 of slide 76. Slide 76 is translated, in a direction shown by arrow O in FIG. 3, to cause extensions 72, 74 to rotate and contract, in a direction shown by arrows P, to the closed orientation to capture FAS 200 and/or SAS 600, which can include a locked configuration of sleeve 52 with a bone screw. In the closed orientation, pins 73 are seated in at the top of slots 75. In some embodiments, extensions 72, 74 are flexible to facilitate contraction.

Sleeve 52 includes a surface 60 that defines a channel 62. Channel 62 is configured for disposal of slide 76, as described herein. Sleeve 52 is engageable with an adaptor 50, as described herein, such that adaptor 50 is pivotable and/or rotatable relative to sleeve 52, FAS 200 and/or SAS 600. Rotation of adaptor 50 facilitates engagement of adaptor 50 with compressor/distractor 250, as described herein.

Sleeve 52 includes a capture portion 64 configured to connect stick 12 with a receiver of FAS screw 200 (FIG. 9) and/or SAS 600 (FIG. 10). Positioning of stick 12 with an arm of receiver 202 or receiver 602 provides for direct access to receiver 202 or receiver 602 to facilitate insertion of rod 210. In some embodiments, stick 12 is connected with a receiver at a point of rotation at the receiver level. In some embodiments, one or more sticks 12 are manipulable, as described herein, to provide a counter-torque for small deformity maneuvers and manipulation of vertebrae during a surgical treatment, for example, to displace, pull, twist or align vertebrae.

Figure 2:
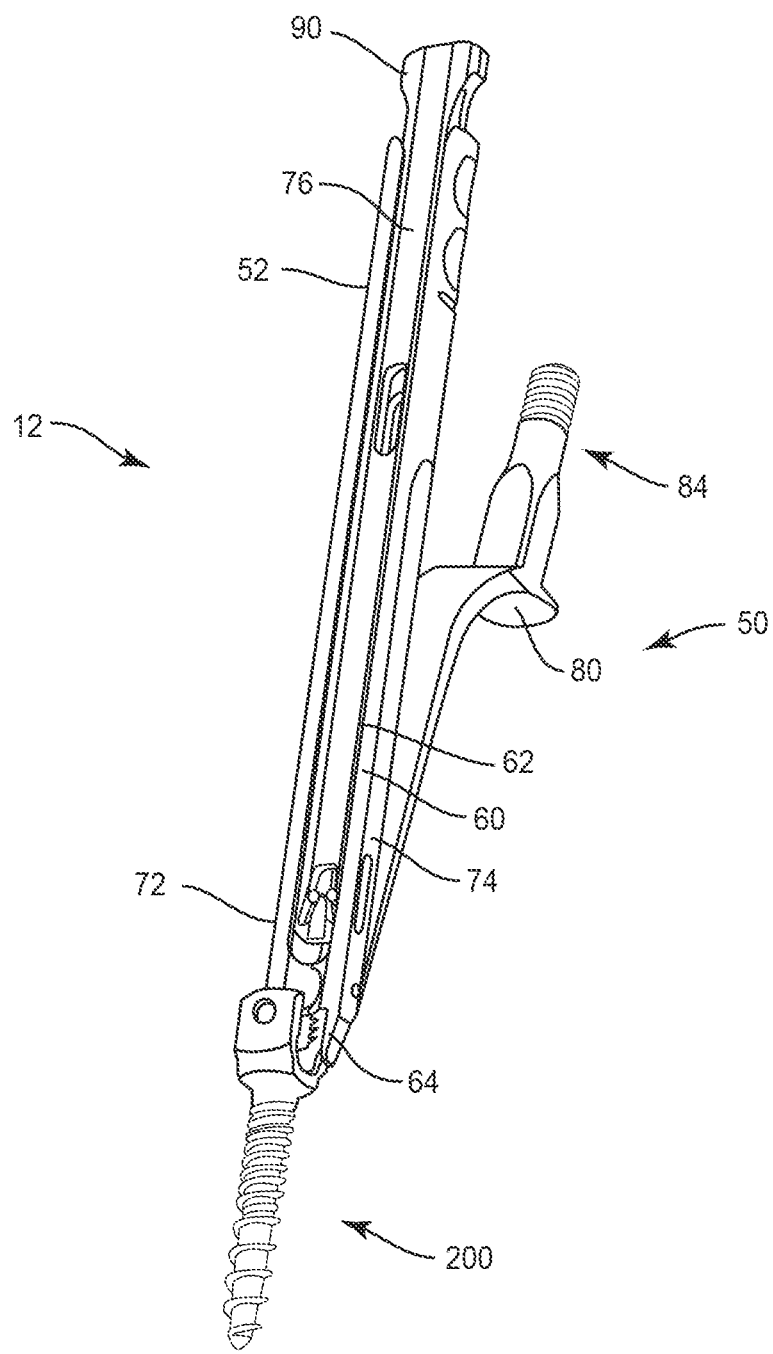
FIG. 2 is a perspective view of components of one embodiment of a surgical system in accordance with the principles of the present disclosure.

Adaptor 50 extends from and is pivotable relative to sleeve 52, as shown in FIGS. 1 and 2. Adaptor 50 extends between an end 54 and an end 56. End 54 is connected to sleeve 52 by a pin hinge 58. Pin 58 facilitates rotation of adaptor 50 relative to sleeve 52, FAS 200 and/or SAS 600. In some embodiments, adaptor 50 may be variously oriented relative to sleeve 52, such as, for example, transverse, perpendicular, angular and/or offset. Rotation of arm 80 facilitates connection of adaptor 50 and sticks 12 with compressor/distractor 250, as described herein.

End 56 includes an arm 80 extending therefrom. In some embodiments, arm 80 is may be variously oriented relative to axis X1, such as, for example, parallel, perpendicular, angular and/or offset. Arm 80 includes a surface 82 that defines a threaded lock surface 84. Surface 84 is engageable with a lock nut 274 to fix compressor/distractor 250 and an angulation module 266 with sticks 12 and adaptors 50, as described herein. In some embodiments, surface 84 may have alternative locking and/or tool engaging surfaces, such as, for example, rectangular, polygonal, hexalobe, oval, irregular, cruciform, phillips, square, polygonal or star cross sectional configuration.

Compressor/distractor 250 includes a longitudinal element, such as, for example, a rack 252, as shown in FIG. 6. Rack 252 extends between an end 254 and an end 256 defining a longitudinal axis A1. Rack 252 is configured to connect adjacent sticks 12. Rack 252 includes an outer surface 258 having a plurality of teeth, such as, for example, splines 260 engageable with an arm 282, as described herein. Rack 252 includes an arm 262 extending from end 254.

Arm 262 includes a surface that defines an opening (not shown) configured for disposal of surface 84 for mounting compressor/distractor 250 with stick 12, angulation module 266 and adaptor 50. Rack 252 includes arm 282 that is axially translatable along axis A1 relative to arm 262. Arm 282 includes a surface that defines an opening (not shown) configured for disposal of surface 84 for mounting compressor/distractor 250 with stick 12, angulation module 266 and adaptor 50.

Compressor/distractor 250 includes a ratchet, which includes splines 260 and arm 282 engageable in a bi-directional and/or two-way ratchet configuration. Arm 282 includes a latch 300 that includes a pinion or pawl (not shown) engageable with splines 260. Latch 300 is pivotable relative to arm 282 for disposal in a distraction position, as shown in FIG. 6. In the distraction position, latch 300 engages rack 252 to allow axial and/or incremental translation of arm 282 relative to arm 262/rack 252, in the direction shown by arrow A, and prevents axial translation of arm 282 relative to arm 262/rack 252, in an opposing direction shown by arrow B. As such, distraction of vertebral tissue connected with sticks 12 can be performed.

Latch 300 is pivotable relative to arm 282 for disposal in a neutral position (not shown). In the neutral position, latch 300 disengages from rack 252 to allow free axial translation of arm 262/rack 252 relative to arm 282. Latch 300 is pivotable relative to arm 282 for disposal in a compression position (not shown). In the compression position, latch 300 engages rack 252 to allow axial and/or incremental translation of arm 282 relative to arm 262/rack 252, in the direction shown by arrow B, and prevents axial translation of arm 282 relative to arm 262/rack 252, in an opposing direction shown by arrow A. As such, compression of vertebral tissue connected with sticks 12 can be performed. In some embodiments, a rotatable key 302 includes a gear surface engageable with splines 260 to axially and/or incrementally translate rack 252 to facilitate distraction and/or compression, as described herein.

Angulation modules 266 are connectable with compressor/distractor 250, sticks 12 and adaptor 50, as shown in FIG. 6. Module 266 includes a surface that defines an opening (not shown) configured for disposal of surface 84 for mounting module 266 with compressor/distractor 250, sticks 12 and adaptor 50. Module 266 includes a body 267 that extends between an end 268 and an end 270. Module 266 includes a longitudinal element, such as, for example, a rack 280, as shown in FIG. 6. Rack 280 includes an outer surface having a plurality of teeth, such as, for example, splines 284.

Rack 280 includes spaced apart arms 290 that define a cavity 292. Arms 290 are configured for capture of sticks 12. Modules 266 are fixed with sticks 12 to allow for angulation and/or correction of vertebral tissue connected with sticks 12, individually, in combination or simultaneously. In some embodiments, engagement of sticks 12 with module 266 facilitates manipulation of vertebrae attached with sticks 12 through an angular range of 0 through 20 degrees of correction and/or relative to an initial orientation of vertebrae.

Body 267 includes a ratchet, which includes splines 284 and a latch 286 engageable in a bi-directional and/or two-way ratchet configuration. Latch 286 includes a slider 288 and a lever 294 having a pinion or pawl (not shown)

engageable with splines 284. Slider 288 engages lever 294, which is pivotable relative to body 267 for disposal in a lordosis position, as shown in FIG. 6. In the lordosis position, the pawl of lever 294 engages rack 280 in an orientation to allow axial and/or incremental translation of rack 280 relative to body 267, in the directions shown by arrows C, and prevents axial translation of rack 280 relative to body 267, in opposing directions shown by arrows D. As such, angulation of vertebral tissue connected with sticks 12 to achieve lordosis can be performed.

Slider 288 is engageable with lever 294, which is pivotable relative to body 267 in an opposing orientation for disposal in a kyphosis position. In the kyphosis position, the pawl of lever 294 engages rack 280 in an orientation to allow axial and/or incremental translation of rack 280 relative to body 267, in the directions shown by arrows D, and prevents axial translation of rack 280 relative to body 267, in opposing directions shown by arrows C. As such, angulation of vertebral tissue connected with sticks 12 to achieve kyphosis can be performed.

In some embodiments, connection of module 266 with adaptor 50 and sticks 12 facilitates correction of a vertebral angle of vertebrae, for example, to achieve a selected lordosis and/or kyphosis, via manipulation of modules 266, as described herein. In some embodiments, modules 266 are manipulated to manually correct a vertebral angle of vertebrae by pivoting sticks 12. In some embodiments, modules 266 are connected with adaptor 50, compressor/distractor 250 and/or sticks 12 to maintain a corrected vertebral angle of vertebrae during distraction and/or compression, as described herein.

Figure 5:
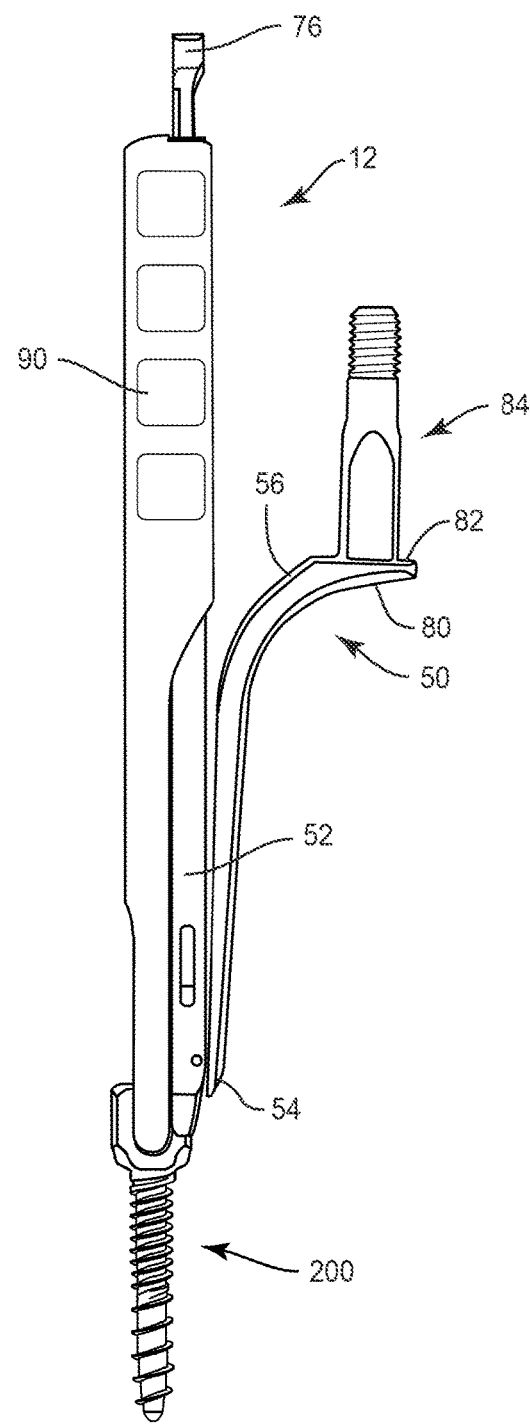
FIG. 5 is a side view of components of one embodiment of a surgical system in accordance with the principles of the present disclosure.
Figure 27:
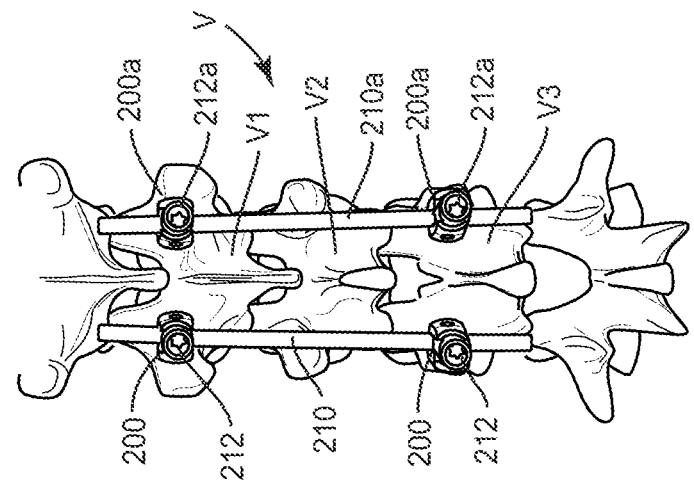
FIG. 27 is a side view of components of one embodiment of a surgical system in accordance with the principles of the present disclosure disposed with vertebrae.

Surgical system 10 includes an alignment guide 90, as shown in FIG. 5. Guide 90 is configured for disposal with a receiver of FAS 200 and/or SAS 600 to orient stick 12 and facilitate identifying, locating and/or engaging stick 12 with the receiver of FAS 200 and/or SAS 600. FAS 200 includes a receiver 202 having a pair of spaced apart arms 204, 204*a*, as shown in FIG. 9. Receiver 202 is configured for engagement with sticks 12, as described herein. Arms 204, 204*a* include an inner surface that defines a U-shaped passageway 206 for disposal of a spinal rod 210, as described herein. The inner surface of receiver 202 includes a thread form configured for engagement with a set screw 212 (FIG. 27). Set screw 212 is threaded with receiver 202 to attach, fix and/or connect rod 210 with FAS 200 including a shaft 208 attached with tissue to facilitate connection of the tissue with surgical instruments for a correction treatment, as described herein. SAS 600 has a receiver 602, as shown in FIG. 10. Receiver 602 is configured for engagement with sticks 12, as described herein and includes a shaft 608 configured for penetrating tissue. Receiver 602 includes a saddle 603 that is selectively translatable within receiver 602 in a sagittal plane to accommodate sagittal anatomical differences. The saddle receives and movably supports rod 210 such that rod 210 is movable within receiver 602 through an angular range.

In assembly, operation and use, surgical system 10, similar to the systems and methods described herein, is employed with a surgical procedure for treatment of a spine of a patient including vertebrae V, as shown in FIGS. 7-29. Surgical system 10 is employed with a procedure for treatment of an applicable condition or injury of an affected section of a spinal column and adjacent areas within a body. For example, vertebrae V includes a vertebral level V1, a vertebral level V2 and a vertebral level V3, as shown in FIGS. 7 and 8. Diseased and/or damaged vertebrae and intervertebral discs are disposed at vertebra V2 between vertebrae V1 and V3. In some embodiments, components of surgical system 10 are configured for insertion with a vertebral space to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, surgical system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient and a cutting instrument (not shown) creates a surgical pathway for implantation of components of surgical system 10. A preparation instrument (not shown) can be employed to prepare tissue surfaces of vertebrae V, as well as for aspiration and irrigation of a surgical region.

Figure 13:
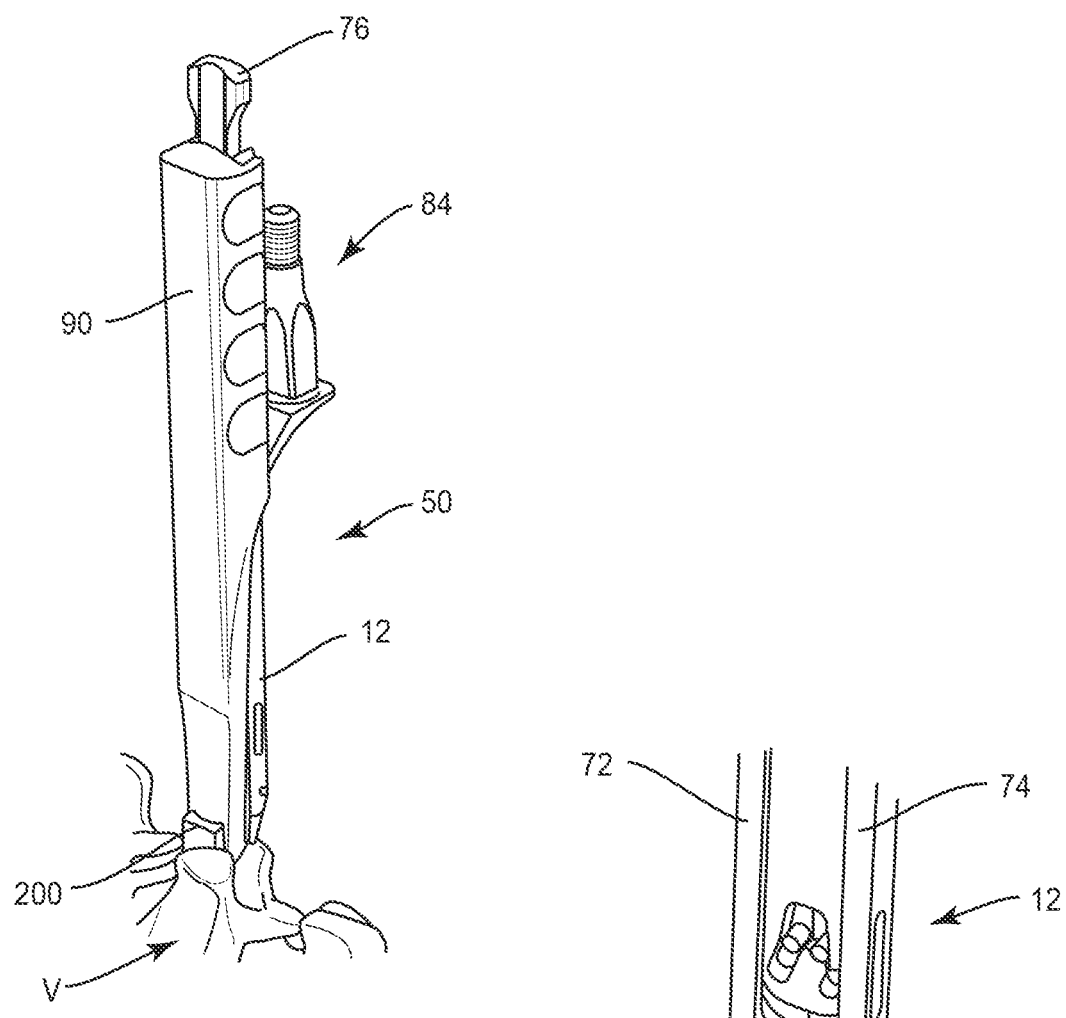
FIG. 13 is a perspective view of components of one embodiment of a surgical system in accordance with the principles of the present disclosure disposed with vertebrae.
Figure 14:
FIG. 14 is a perspective view of components of one embodiment of a surgical system in accordance with the principles of the present disclosure disposed with vertebrae.

Pilot holes or the like are made in selected vertebrae V1 and V3 for receiving bone screws, such as, for example, FAS 200, 200*a*. A driver (not shown) is disposed adjacent vertebrae V at a surgical site and is manipulated to drive, torque, insert or otherwise connect FAS 200, 200*a* with vertebrae V1 and V3. FAS 200, 200*a* are engaged with vertebrae V along a lateral side L and a contra-lateral side CL of vertebrae V. Sticks 12 are disposed in an open orientation, as described herein, and guide 90, as shown in FIG. 13, is connected with each stick 12/adaptor 50 and inserted along the surgical pathway to locate each stick 12/adaptor 50 with FAS 200, 200*a*, as described herein. Sticks 12/adaptors 50 are engaged with FAS 200 and sticks 12*a*/adaptors 50 are engaged with FAS 200*a*. Sticks 12, 12*a* are disposed in a closed orientation, as described herein and shown in FIGS. 11, 12 and 14, to capture FAS 200, 200*a*.

Figure 15:
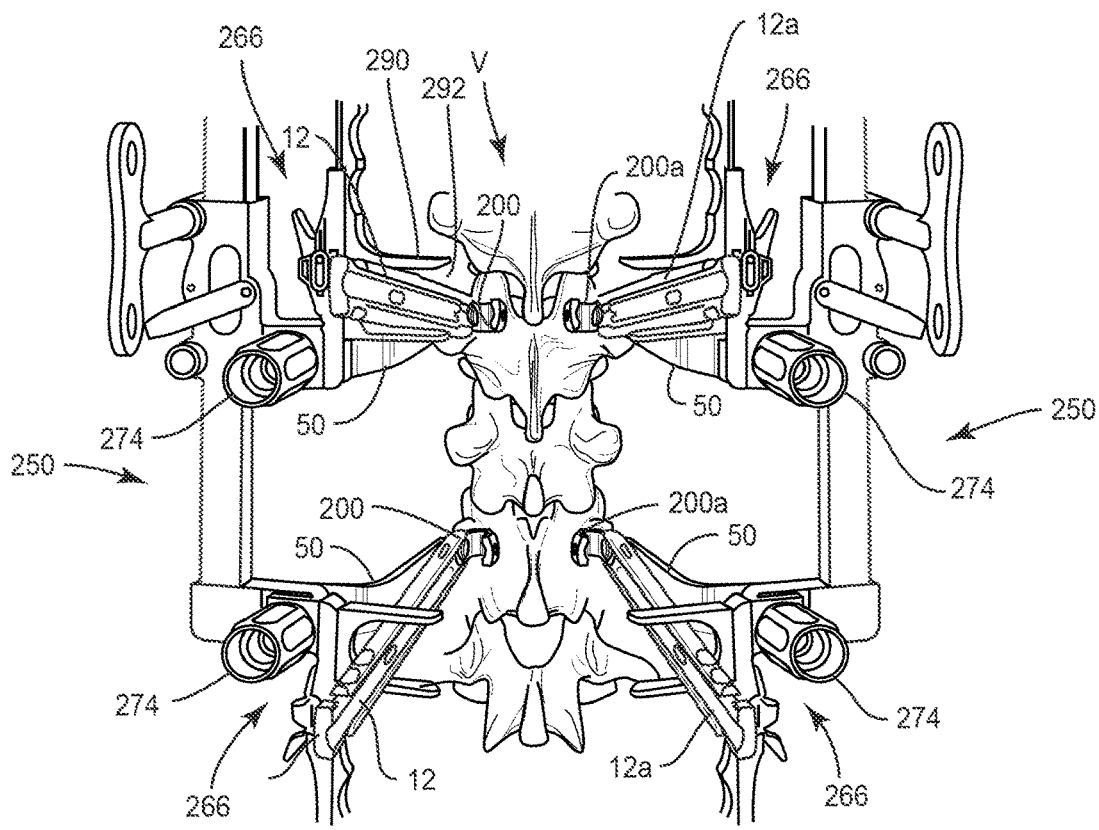
FIG. 15 is a plan view of components of one embodiment of a surgical system in accordance with the principles of the present disclosure disposed with vertebrae.
Figure 16:
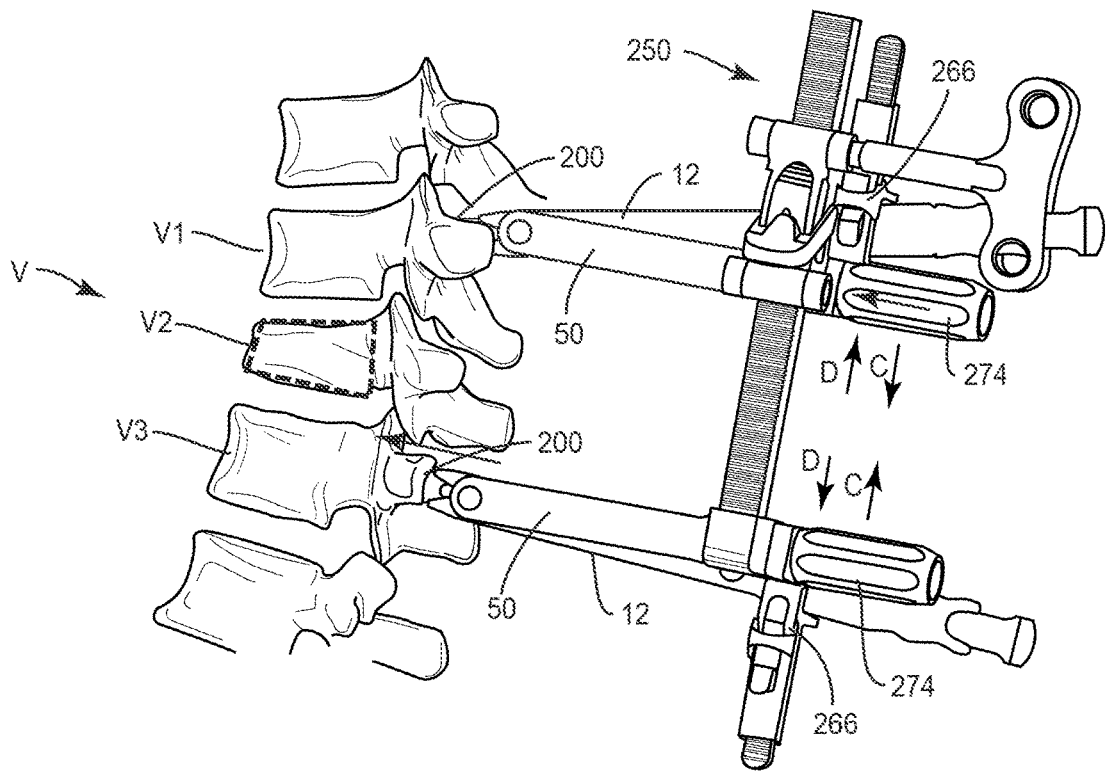
FIG. 16 is a side view of components of one embodiment of a surgical system in accordance with the principles of the present disclosure disposed with vertebrae.
Figure 19:
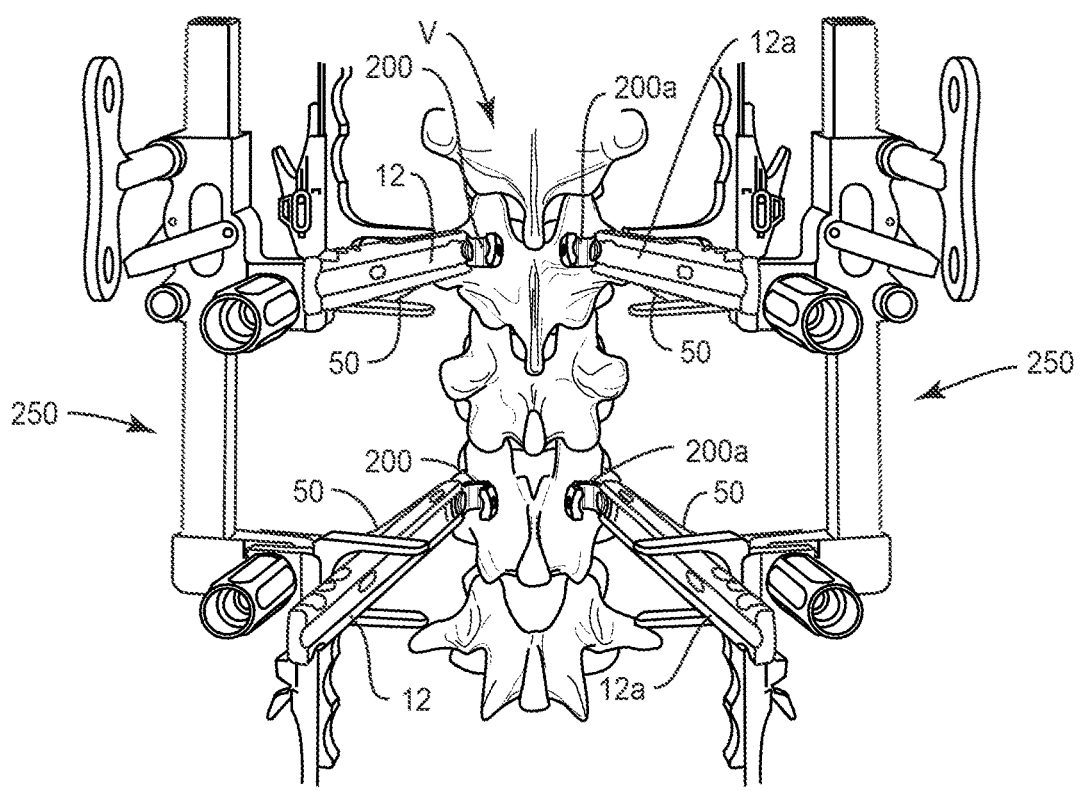
FIG. 19 is a plan view of components of one embodiment of a surgical system in accordance with the principles of the present disclosure disposed with vertebrae.
Figure 20:
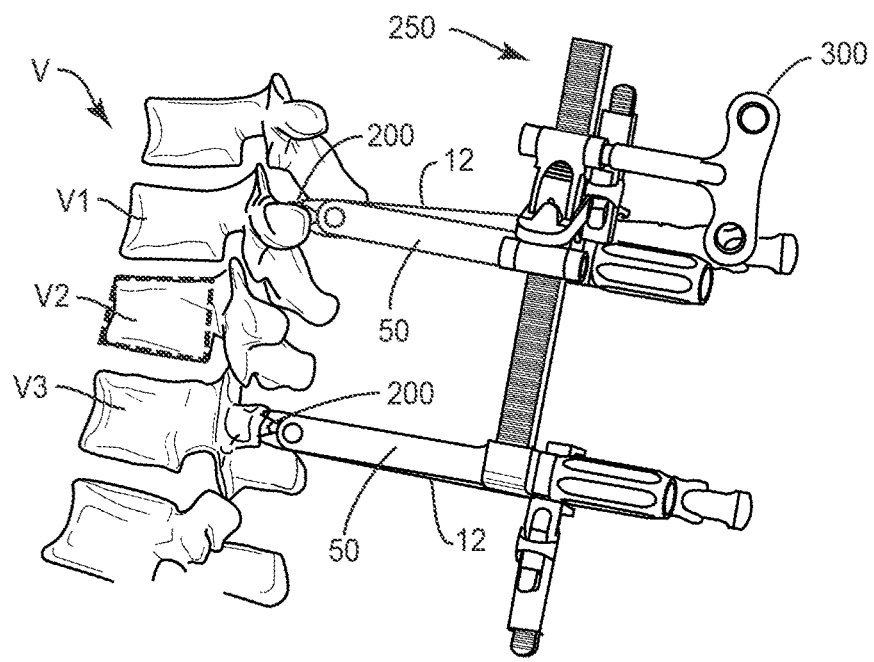
FIG. 20 is a side view of components of one embodiment of a surgical system in accordance with the principles of the present disclosure disposed with vertebrae.

Compressor/distractor 250 and modules 266 are mounted with sticks 12, 12*a*/adaptors 50 via surface 84 and lock nut 274 for fixation therewith, as described herein and shown in FIGS. 15 and 16. Arms 290 of modules 266 capture sticks 12, 12*a*/adaptors 50, as described herein. Modules 266 are fixed with sticks 12, 12*a*/adaptors 50, to allow for angulation and/or correction of vertebrae V connected with sticks 12, 12*a*/adaptors 50. For example, latch 286 of module 266 is disposable in a lordosis position, as described herein, to allow translation of rack 280, in the directions shown by arrows C, and prevent translation of rack 280, in the directions shown by arrows D, relative to body 267. As such, angulation of vertebrae V1, V3 connected with sticks 12, 12*a*/adaptors 50 to achieve a selected lordosis can be performed. Module 266 prevents translation of rack 280, in the directions shown by arrows D, relative to body 267 to maintain the selected lordosis during distraction and/or compression, as described herein. In some embodiments, as shown in FIGS. 19 and 20, correction and/or angulation of vertebrae V1, V3 can be performed directly with sticks 12, 12*a*/adaptors 50 and modules 266 maintain the selected correction and/or angulation of vertebrae V1, V3.

Figure 17:
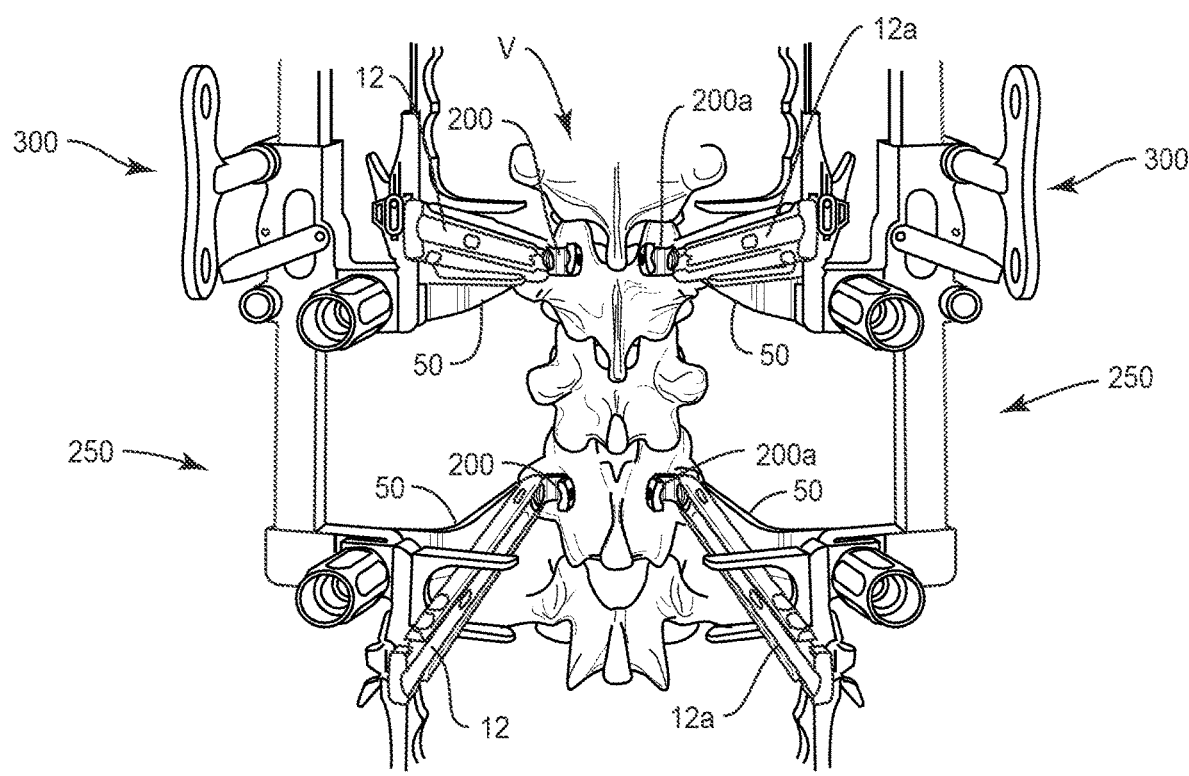
FIG. 17 is a plan view of components of one embodiment of a surgical system in accordance with the principles of the present disclosure disposed with vertebrae.
Figure 18:
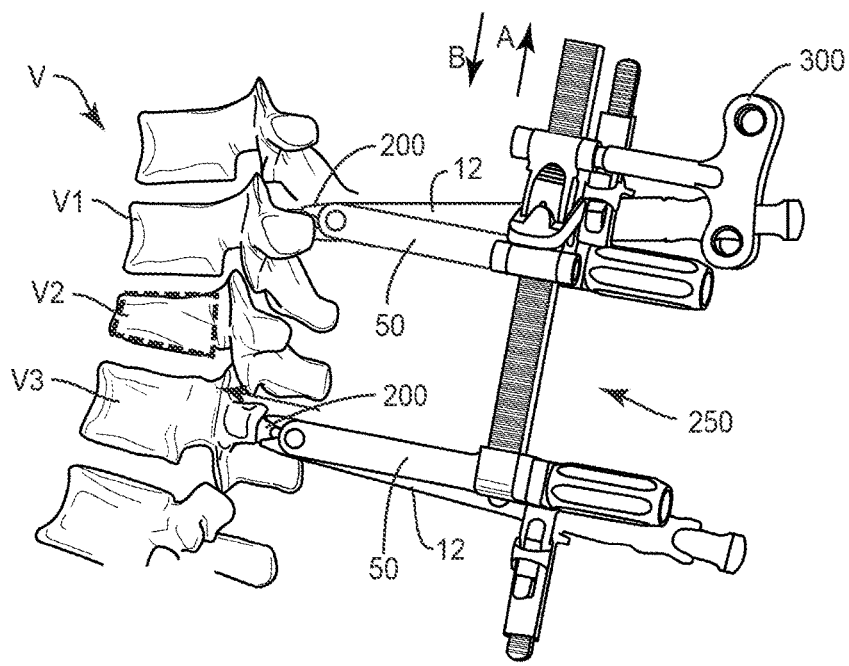
FIG. 18 is a side view of components of one embodiment of a surgical system in accordance with the principles of the present disclosure disposed with vertebrae.

Compressor/distractor 250 is connected with sticks 12, 12*a*/adaptors 50, to allow for distraction and/or compression of vertebrae V connected with sticks 12, 12*a*/adaptors 50, as described herein and shown in FIGS. 17 and 18. For example, latch 300 is pivotable to the distraction position, as described herein, to allow translation of arm 282, in the direction shown by arrow A, and prevent translation of arm 282, in the direction shown by arrow B, relative to arm 262/rack 252. As such, distraction of vertebrae V1, V3 connected with sticks 12, 12a/adaptors 50 can be performed. A key 302 is engageable with splines 260 to translate rack 252 for distraction. In some embodiments, keys 302 can simultaneously engage compressor/distractors 250 connected with vertebrae V on sides L, CL to perform parallel distraction of vertebrae V1, V3.

Figure 21:
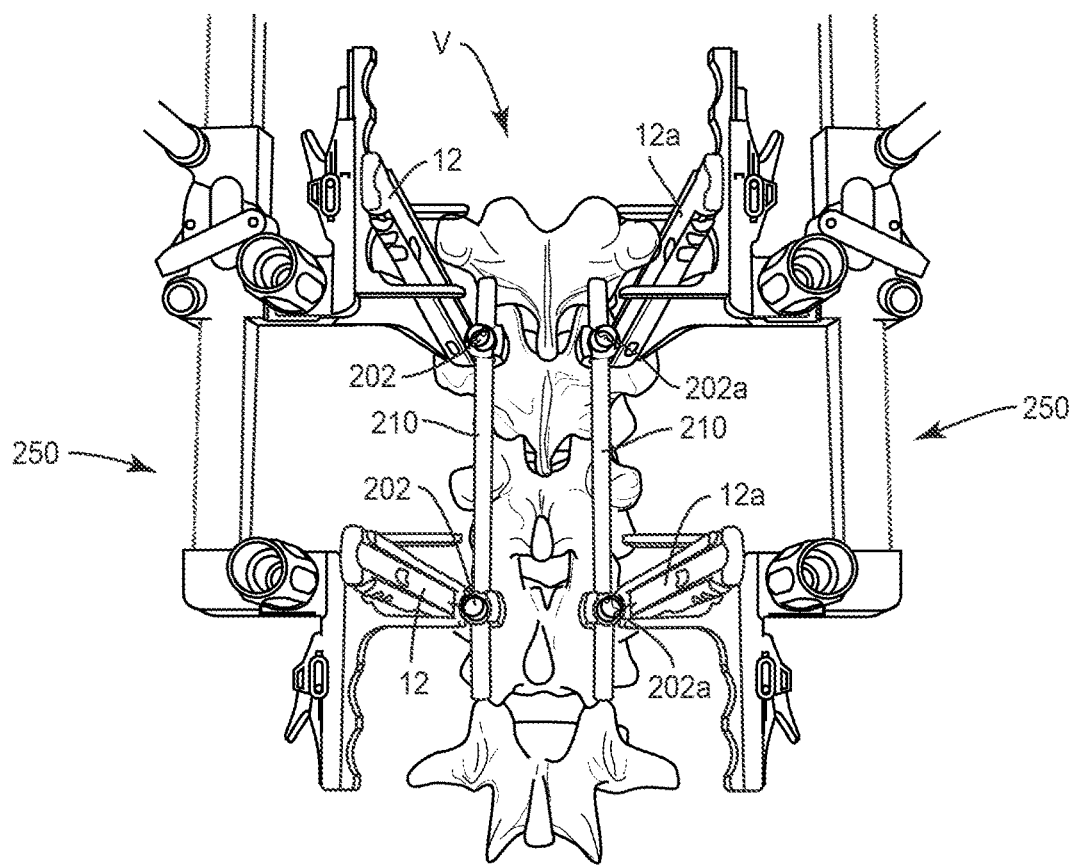
FIG. 21 is a plan view of components of one embodiment of a surgical system in accordance with the principles of the present disclosure disposed with vertebrae.
Figure 22:
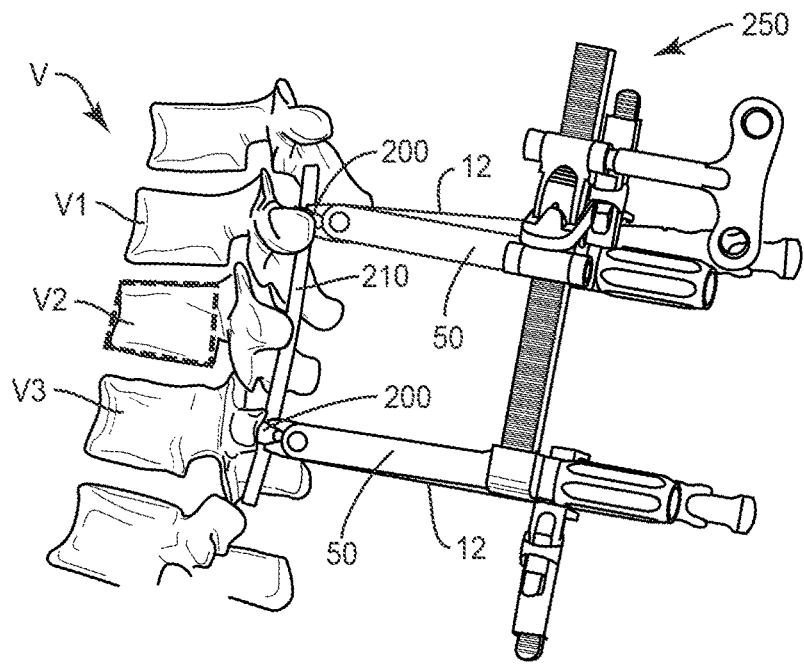
FIG. 22 is a side view of components of one embodiment of a surgical system in accordance with the principles of the present disclosure disposed with vertebrae.
Figure 23:
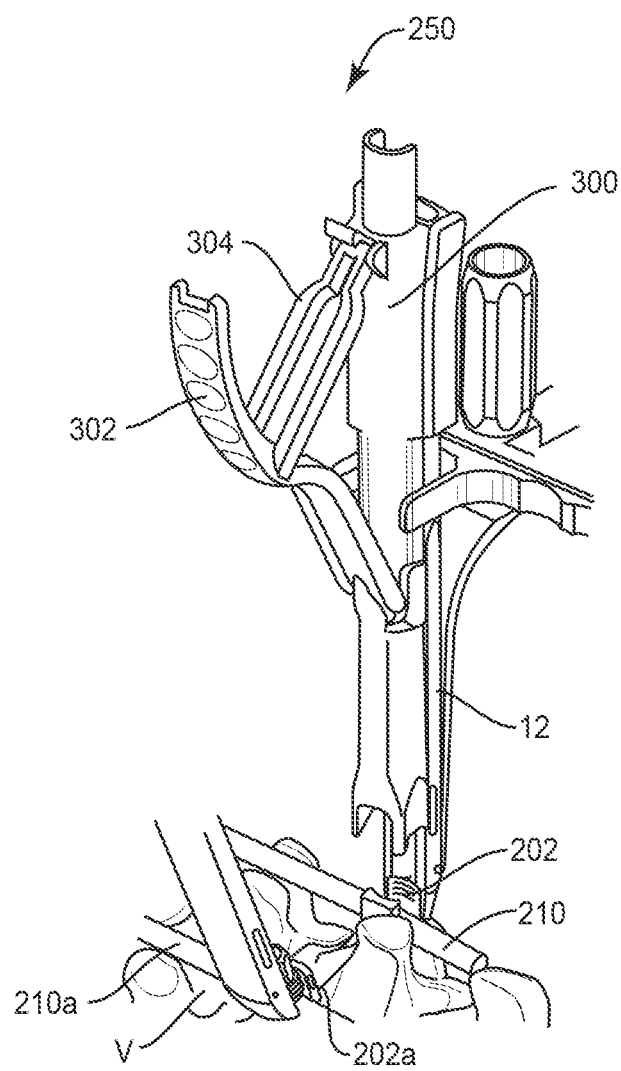
FIG. 23 is a perspective view of components of one embodiment of a surgical system in accordance with the principles of the present disclosure disposed with vertebrae.
Figure 24:
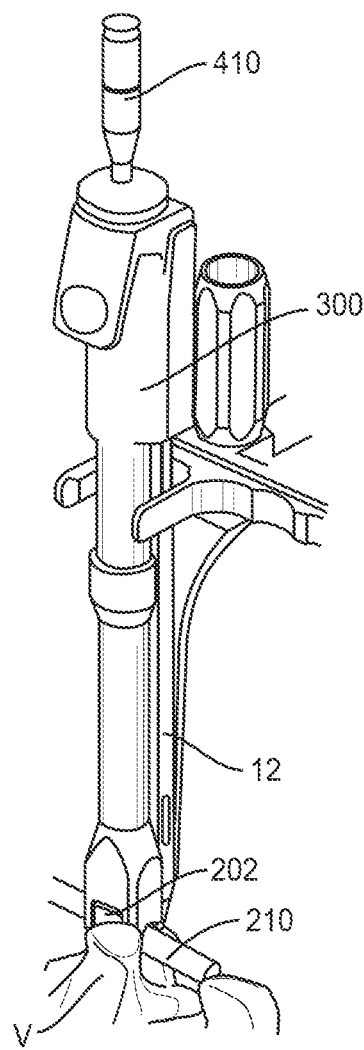
FIG. 24 is a perspective view of components of one embodiment of a surgical system in accordance with the principles of the present disclosure disposed with vertebrae.
Figure 26:
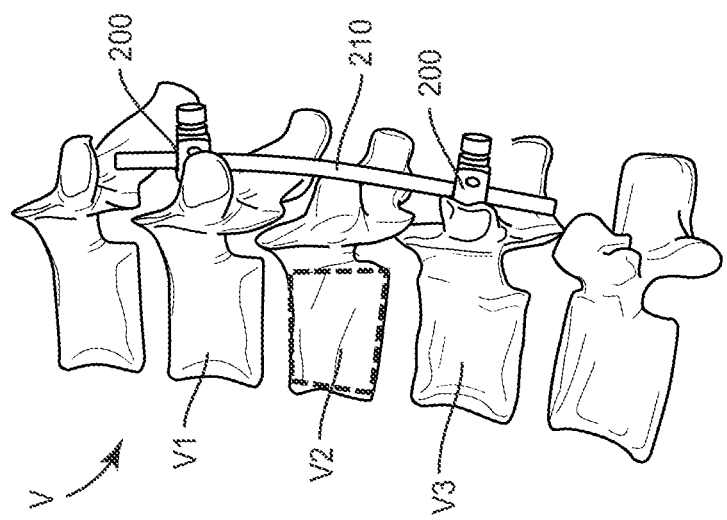
FIG. 26 is a side view of components of one embodiment of a surgical system in accordance with the principles of the present disclosure disposed with vertebrae.
Figure 25:
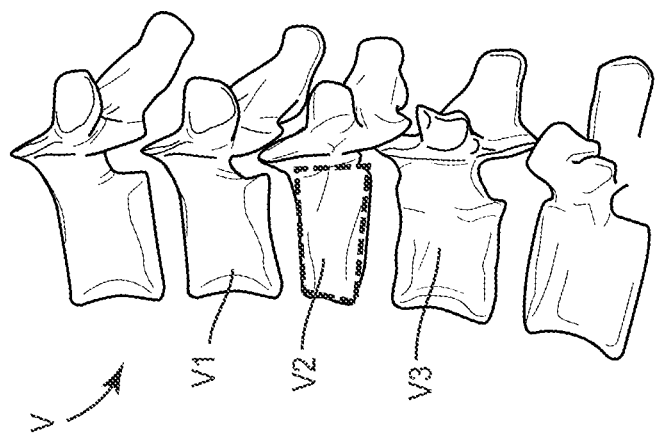
FIG. 25 is a side view of vertebrae.

Rod 210 is contoured and disposed within receivers 202, 202a, as shown in FIGS. 21 and 22. A surgical instrument, such as, for example, a rod reducer 300 is translated into engagement with rods 210, 210a to reduce rods 210, 210a with receivers 202, 202a. In some embodiments, as shown in FIG. 23, rod reducer 300 is attachable with compressor/distractor 250 and includes a lever 302 having a linkage 304 that is manipulable for rotation to seat and/or reduce rods 210, 210a with receivers 202, 202a. In some embodiments, as shown in FIG. 24, rod reducer 300 is attachable with compressor/distractor 250 and includes a screw/threaded longitudinal driver 410 that is rotatable to incrementally translate and seat and/or reduce rods 210, 210a with receivers 202, 202a. Driver 410 is inserted with set screws 212 to fix rod 210 with FAS 200. Vertebrae V is aligned to a selected orientation for correction, as shown in FIGS. 25-27.

Figure 28:
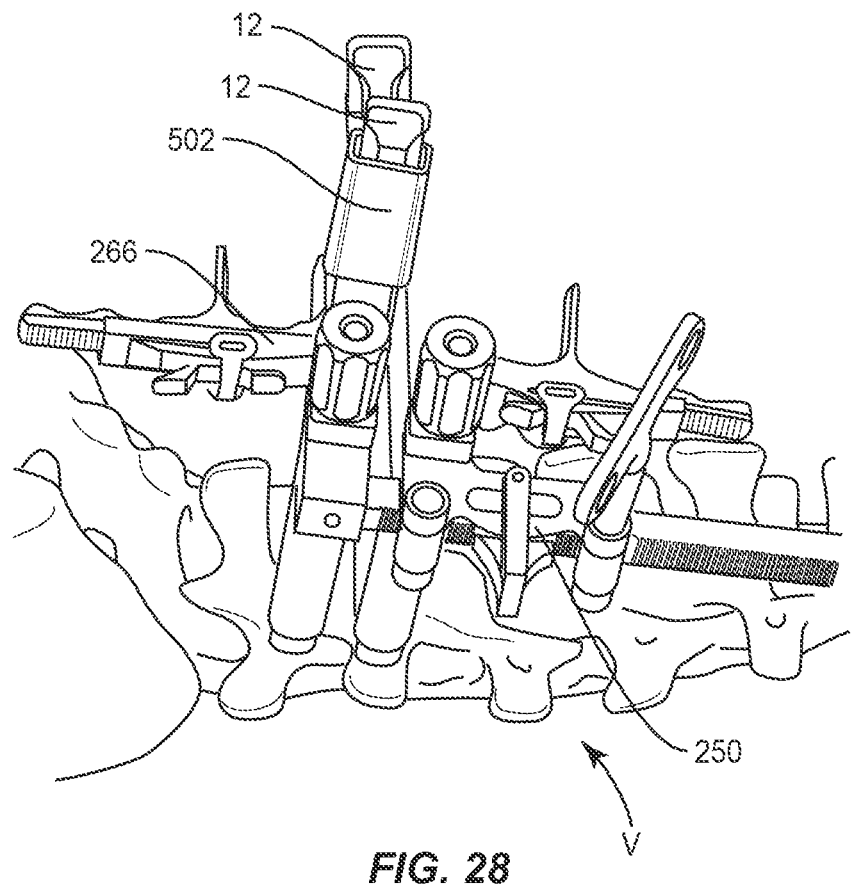
FIG. 28 is a perspective view of components of one embodiment of a surgical system in accordance with the principles of the present disclosure disposed with vertebrae.
Figure 29:
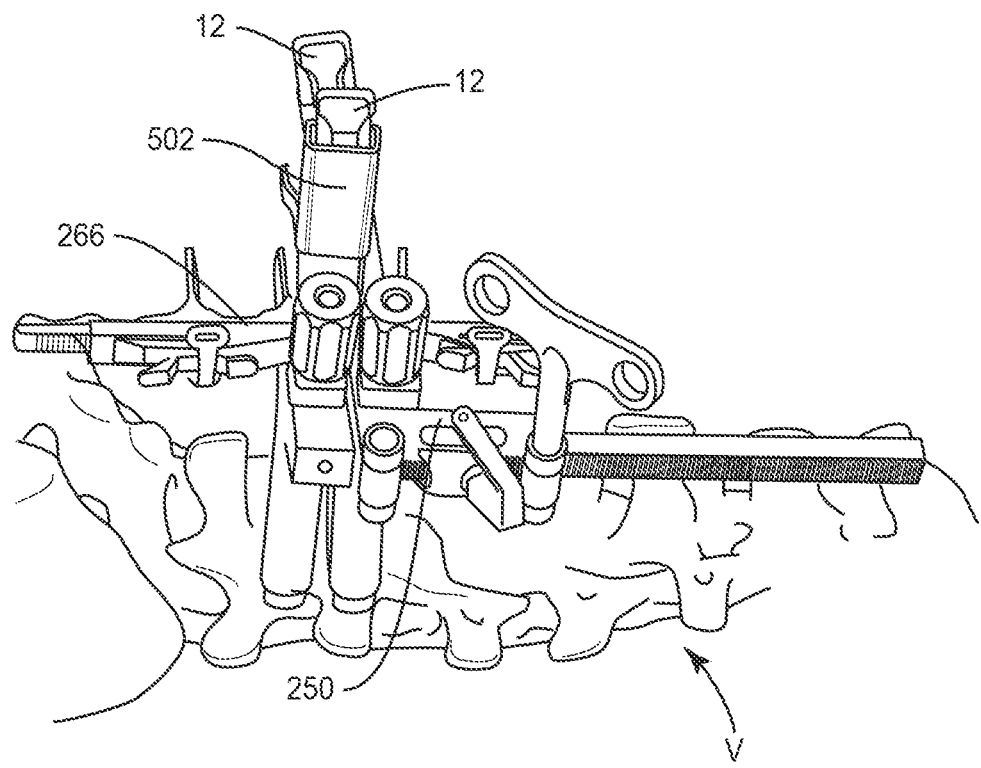
FIG. 29 is a perspective view of components of one embodiment of a surgical system in accordance with the principles of the present disclosure disposed with vertebrae.

In some embodiments, as shown in FIGS. 28 and 29, surgical system 10, similar to the systems and methods described herein, can be employed with a degenerative fusion to facilitate decompression, interbody access and interbody implant. For example, to distract vertebrae V, facilitate interbody access and implant insertion, modules 266 are disposed outside of sticks 12 and compressor/distractor 250 is disposed in a distraction position to distract vertebrae V. Following decompression of a portion of vertebrae V, interbody access and implant insertion, compressor/distractor 250 is disposed in a neutral position, as described herein, and sticks 12 are crossed. A crossing block 502 captures the crossed sticks 12. Compressor/distractor 250 is disposed in a compression position, as described herein, and key 302 is rotated to selectively compress vertebrae V.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

In some embodiments, surgical system 10 includes one or a plurality of alternate surgical instruments, each configured for mating engagement in a quick release configuration with spinal constructs, as described herein. This configuration facilitates the interchangeability of the spinal constructs with the alternate surgical instruments. In some embodiments, surgical system 10 includes one or a plurality of alternate surgical instruments, such as, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

The invention claimed is:

1. A surgical system comprising:
 a first fastener comprising a receiver and a shaft configured to be fixed with vertebral tissue, the receiver comprising spaced apart first and second arms;
 at least one implant support including a first implant support having a first longitudinal member and a second longitudinal member that simultaneously engage the first arm such that the at least one implant support is spaced apart from the second arm, the longitudinal members each including a pin, the first implant support comprising a translation element positioned in a channel of each of the longitudinal members, the pins being disposed in slots of the translation element such that translation of the translation element relative to the longitudinal members rotates the longitudinal members relative to one another to move the first implant support between an open orientation and a closed orientation to capture the first arm; and
 at least one adaptor including a first adaptor extending longitudinally along and being engageable with the first implant support,
 the first adaptor being rotatable relative to the first implant support to connect the first implant support with a surgical instrument to manipulate the vertebral tissue.

2. A surgical system as recited in claim 1, wherein the first arm includes a first end surface and an opposite second end surface, the first longitudinal member directly engaging the first end surface simultaneously as the second longitudinal member directly engages the second end surface.

3. A surgical system as recited in claim 1, wherein the longitudinal members and the first adaptor are connected via a hinge disposed adjacent a connection with the receiver.

4. A surgical system as recited in claim 1, wherein the translation element extends along a longitudinal axis between opposite proximal and distal ends, the slots each including a distal portion extending at an acute angle relative to the longitudinal axis.

5. A surgical system as recited in claim 1, further comprising an alignment guide that mates with the receiver of the first fastener and is connectable with the first implant support.

6. A surgical system as recited in claim 1, further comprising an angulation module connected to the first adaptor, the first implant support and the surgical instrument.

7. A surgical system as recited in claim 6, wherein the angulation module is connected with the first implant support to rotate the first implant support and the vertebral tissue.

8. A surgical system as recited in claim 6, wherein the angulation module engages the first implant support to fix the first implant support and the vertebral tissue connected therewith at a selected angular orientation relative to the surgical instrument.

9. A surgical system as recited in claim 6, wherein the angulation module includes a ratchet.

10. A surgical system as recited in claim 1, further comprising a second implant support engageable with a receiver of a second fastener, the second fastener having a shaft configured to be fixed with the tissue, and a second adaptor extending longitudinally along and being engageable with the second implant support, the adaptors being oriented to releasably engage the surgical instrument to distract and/or compress vertebral tissue.

11. A surgical system as recited in claim 1, wherein the surgical instrument includes a ratchet.

12. A surgical system as recited in claim 1, wherein the surgical instrument includes a ratchet that prevents movement in a first direction and a second direction.

13. A surgical system as recited in claim 1, further comprising a rod reducer that is connectable with the first implant support.

14. A surgical system as recited in claim 13, wherein the rod reducer includes a lever linkage that translates a surface of the rod reducer into engagement with a spinal rod.

15. A surgical system as recited in claim 13, wherein the rod reducer includes a threaded member that translates a surface of the rod reducer into engagement with a spinal rod.

16. A surgical adaptor comprising:
a first fastener comprising a receiver and a shaft configured to be fixed with vertebral tissue, the receiver comprising spaced apart first and second arms;
at least one implant support including a first implant support having a first longitudinal member and a second longitudinal member simultaneously engaging the first arm such that the at least one implant support is spaced apart from the second arm, the longitudinal members each including a pin, the first implant support comprising a translation element positioned in a channel of each of the longitudinal members, the pins being disposed in slots of the translation element such that translation of the translation element relative to the longitudinal members rotates the longitudinal members relative to the translation element to move the first implant support between an open orientation and a closed orientation to capture the first arm; and
at least one adaptor including a first adaptor extending longitudinally along and being engageable with the first implant support, the longitudinal members and the first adaptor being connected via a hinge disposed adjacent a connection with the receiver,
the first adaptor being rotatable relative to the first implant support to connect the first implant support with a surgical instrument to manipulate the vertebral tissue.

17. A surgical adaptor as recited in claim 16, wherein the translation element extends along a longitudinal axis between opposite proximal and distal ends, the distal end including the slots, the slots each including a proximal portion extending parallel to the longitudinal axis and a distal portion extending at an acute angle relative to the longitudinal axis.

18. A surgical adaptor as recited in claim 17, further comprising an alignment guide that mates with the receiver of the first fastener and is connectable with the first implant support.

19. A surgical adaptor comprising:
a first fastener comprising a receiver and a shaft configured to be fixed with vertebral tissue, the receiver comprising spaced apart first and second arms;
at least one implant support including a first implant support having a first longitudinal member and a second longitudinal member that simultaneously engage the first arm such that the at least one implant support is spaced apart from the second arm, the longitudinal members each including a pin, the first implant support comprising a slide positioned in channels of the longitudinal members, the pins being disposed in slots of the slide such that translation of the slide relative to the longitudinal members rotates the longitudinal members relative to the slide to move the first implant support between an open orientation and a closed orientation to capture the first arm;
at least one adaptor including a first adaptor extending longitudinally along and being engageable with the first implant support, the first adaptor being rotatable relative to the first implant support to connect the first implant support with a surgical instrument to distract and/or compress the vertebral tissue; and
an angulation module connected to the first adaptor, the first implant support and the surgical instrument.

20. A surgical adaptor as recited in claim 19, wherein the angulation module is configured to be connected with the first implant support and to rotate the first implant support and the vertebral tissue.

\* \* \* \* \*